United States Patent [19]
Cunningham et al.

[11] Patent Number: 6,160,104
[45] Date of Patent: Dec. 12, 2000

[54] MARKERS FOR PEROXISOMAL PROLIFERATORS

[75] Inventors: Mary Jane Cunningham, Sunnyvale; Gary B. Zweiger, San Mateo; Scott R. Panzer, Sunnyvale; Jeffrey J. Seilhamer, Los Altos Hills, all of Calif.

[73] Assignee: Incyte Pharmaceuticals, Inc., Palo Alto, Calif.

[21] Appl. No.: 09/172,108

[22] Filed: Oct. 13, 1998

[51] Int. Cl.$^7$ .......................... C07H 21/04; C07H 21/00; C12Q 1/68; C12P 19/34; C12M 1/34

[52] U.S. Cl. ...................... 536/23.1; 435/6; 435/91.1; 435/287.2; 536/23.2; 536/24.3; 536/24.31; 536/24.32; 536/24.33

[58] Field of Search .......................... 435/6, 91.1, 285.1, 435/287.2; 536/23.1, 22.1, 24.3, 24.31, 24.32, 24.33

[56] References Cited

U.S. PATENT DOCUMENTS 5,073,677  12/1991  Helmer et al. .

OTHER PUBLICATIONS

Wrighton et al Mol.Pharmacology vol. 28 pp. 312–321, 1985.

Kirita et al ARch. Biochem Biophys. vol. 307 (2) pp. 253–258, 1993.

Stromstredt et al DNA and Cell Biology vol. 9, No. 8, pp. 569–577, 1990.

Schena, M., et al., Parallel human genome analysis: Microarray–based expression monitoring of 1000 genes, *Proc. Natl. Acad. Sci. USA*, 93:10614–10619, (Oct. 1996).

Degawa, M., Metabolic Activation and Carcinogen–DNA Adduct Detection in Human Larynx, *Cancer Research*, 54:4915–4919, (Sep. 15, 1994).

Qu, et al, Formation and persistence of DNA adducts in different target tissues of rats after multiple administration of benzo[a] pyrene, *Carcinogenesis*, 17:1, 53–59, (1996).

Chen, W., et al, Oxidation of Acetaminophen to its Toxic Quinone Imine and Nontoxic Catechol Metabolites by Baculovirus–Expressed and Purified Human Cytochromes P450 2E1 and 2A6, *Chem. Res. Toxicol.*, 11:295–301, (1998).

Kroger, H., et al., Protection from Acetaminophen–Induced Liver Damage by the Synergistic Action of Low Doses of the Poly(ADP–ribose) Polymerase–Inhibitor Nicotinamide and the Antioxidant N–Acetylcysteine or the Amino Acid L–Methionine, *Gen. Pharmac.*, 28:2, 257–263, (1997).

Lock, E., et al., Biochemical Mechanisms of Induction of Hepatic Peroxisome Proliferation, *Annu. Rev. Pharmacol. Toxicol.*, 29:145–63, (1989).

Kawashima, H., et al., Protein Expression, Characterization, and Regulation of CYP4F4 and CYP4F5 Cloned from Rat Brain, *Archives of Biochemistry and Biophysics*, 347:1, 348–154, (Nov. 1, 1997).

*Primary Examiner*—W. Gary Jones
*Assistant Examiner*—Jeffrey Siew
*Attorney, Agent, or Firm*—Incyte Genomics, Inc.

[57] ABSTRACT

The present invention relates to a composition comprising a plurality of polynucleotide targets. The composition can be used as hybridizable array elements in a microarray. The present invention also relates to methods for screening compounds and therapeutic treatments for toxicological responses.

8 Claims, No Drawings

SEQUENCE LISTING

<160> NUMBER OF SEQ ID NOS: 56

<210> SEQ ID NO 1
<211> LENGTH: 299
<212> TYPE: DNA
<213> ORGANISM: Homo sapiens
<220> FEATURE: -
<223> OTHER INFORMATION: 700059105H1

<400> SEQUENCE: 1

```
tcatcacaac ccaactgtgt ggccaaatcc agaggtgttt gacccttatc gatttgcacc      60
agagtcttcc cgacacagcc actcattcct gcccttctca ggaggagcaa ggaactgcat     120
tgggaaacag tttgccatga atgaactgaa ggtggccgtg gccctgaccc tgctccgctt     180
tgagctgctg ccagatccca ccaggatccc aatccccata ccaagactcg tgttgaagtc     240
```

```
caagaatggg atctacctgc gtctcaaaaa gctccaataa tcttgacagc acaagacag      299
```

<210> SEQ ID NO 2
<211> LENGTH: 300
<212> TYPE: DNA
<213> ORGANISM: Homo sapiens
<220> FEATURE: -
<223> OTHER INFORMATION: 700059610H1

<400> SEQUENCE: 2

```
aaacaacctg actttcttgc gtgtgaggag tgccttttat gggaacagca tcatctacaa       60
tatgtcctct gatggccgtt tgtcccgccg ggcctgccag attgctcatg agcacacaga      120
tggagtgatc aaaatgagga aggctcagct gcagaatgag gaagagcttc agaaggccag      180
gaagaagagg cacttggatt tcctggacat cctgttgttt gccaaaatgg aggatgggaa      240
gagcttgtct gatgaggacc tgcgtgcaga ggtggacaca ttcatgtttg agggtcatga      300
```

<210> SEQ ID NO 3
<211> LENGTH: 296
<212> TYPE: DNA
<213> ORGANISM: Homo sapiens
<220> FEATURE: -
<223> OTHER INFORMATION: 700059630H1

<400> SEQUENCE: 3

```
gggtttctct gtatttaccc ctacaagatc cctggatggt gtctctgggt tcttccaagg       60
ggccttcctg ctcagtctat ttctggtgct gttcaaggca gtccaattct acttacgaag      120
gcaatggctc tcaaggccc tcgagaagtt cccatccacg ccttcccact ggctttgggg       180
ccacgacctg aaggacagag aattccagca ggttcttacg tgggtagaga aattcccagg      240
tgcctgctta cagtggctct cagggagcaa aacacgagtc ctgctctatg accctg         296
```

<210> SEQ ID NO 4
<211> LENGTH: 288
<212> TYPE: DNA
<213> ORGANISM: Homo sapiens
<220> FEATURE: -
<223> OTHER INFORMATION: 700060207H1

<400> SEQUENCE: 4

```
accccctgcat gggatacgtt tctcgacccc agtgcactgg tttctgtcat cccatgaaat      60
tgcagcaagg gcagtctctt ttgtgggaac agattaactc ctacacatga tgtagattca     120
acacctgcca ggaaagcaga agcattactt aagtgtcctg tgaaggcaaa catcaagtca     180
attcagctta tcttgaagag tggcaaacca tgaactccaa atgtcattgt gtgaaactga     240
acgatggtca ttcattccgg tgctgggttt tggaactgct atgccttc                  288
```

<210> SEQ ID NO 5
<211> LENGTH: 307
<212> TYPE: DNA
<213> ORGANISM: Homo sapiens
<220> FEATURE:
<221> NAME/KEY: unsure
<222> LOCATION: 8, 20, 21, 23, 47, 302
<223> OTHER INFORMATION: a or g or c or t, unknown, or other
<220> FEATURE: -
<223> OTHER INFORMATION: 700061625H1

<400> SEQUENCE: 5

```
gggaaganac actggcttan nanttggttc tgagggaagc tctctgngtg gatacatatt       60
```

```
tataggattt gggtgcaacg aactgtgtga ctagttcagt tcaattcagg gagcaggcag    120
aaaccagcag gtattagaag agatgttcta tatacagagt tctgaggcac tgcagattct    180
gaagaattcc ctaaggaagc acctccctga gtccttaaag gttatgggac tgtctccaca    240
tgaaccaggg aaacccattc aagctcaagg ctgtggtgga caagtggctg atttaatact    300 gntgtta                                                              307

<210> SEQ ID NO 6
<211> LENGTH: 97
<212> TYPE: DNA
<213> ORGANISM: Homo sapiens
<220> FEATURE:
<221> NAME/KEY: unsure
<222> LOCATION: 48, 90
<223> OTHER INFORMATION: a or g or c or t, unknown, or other
<220> FEATURE: -
<223> OTHER INFORMATION: 700062809H1

<400> SEQUENCE: 6
ccctgagagt ctccaaaatg tttcagtctg ttataagaac cccattanct cactaaagct    60
tgcactggct gactcctgga cggggttccn gaatgtg                             97

<210> SEQ ID NO 7
<211> LENGTH: 312
<212> TYPE: DNA
<213> ORGANISM: Homo sapiens
<220> FEATURE:
<221> NAME/KEY: unsure
<222> LOCATION: 78
<223> OTHER INFORMATION: a or g or c or t, unknown, or other
<220> FEATURE: -
<223> OTHER INFORMATION: 700063128H1

<400> SEQUENCE: 7
cggtcggtac cggagagcgc aggttgtatc accaacatgg gggactctca cgaagacacc    60
agtgccacca tgcctgangc cgtggctgaa gaagtgtctc tattcagcac gacggacatg    120
gttctgtttt ctctcatcgt gggggtcctg acctactggt tcatctttag aaagaagaaa    180
gaagagatac cggagttcag caagatccaa acaacggccc cacccgtcaa agagagcagc    240
ttcgtggaaa agatgaagaa aacgggaagg aacattatcg tattctatgg ctcccagacg    300
ggaaccgctg ag                                                        312

<210> SEQ ID NO 8
<211> LENGTH: 235
<212> TYPE: DNA
<213> ORGANISM: Homo sapiens
<220> FEATURE: -
<223> OTHER INFORMATION: 700138117H1

<400> SEQUENCE: 8
gaggattcac tcacatttgc ttcccgctgg ccatgagtga gctgcccttt ctgagtccag    60
agggagccag agggcctcac aacaacagag ggtctcagag ctccctggag gaaggctcag    120
ttacaggctc agaggctcgg cacagcttag gtgtcctgaa tgtgtccttc agcgtcagaa    180
ccgtgtcggg ccctggtgga acatcaaatc atgccagcag aagtgggaca ggaaa         235

<210> SEQ ID NO 9
<211> LENGTH: 214
<212> TYPE: DNA
<213> ORGANISM: Homo sapiens
<220> FEATURE: -
<223> OTHER INFORMATION: 700139104H1
```

<400> SEQUENCE: 9

```
gagatgttcc ctgtcatcga acagtatgga gacattttgg taaaatactt gaggcaagag        60
aaaggcaaac ctgtccctgt gaaagaagtg tttggtgcct acagcatgga tgtgatcacc       120
agcacatcat ttggagtgaa tgttgattcc ctcaacaacc cgaaggatcc ttttgtggag       180
aaagccaaga agctcttaag aattgatttt tttg                                   214
```

<210> SEQ ID NO 10
<211> LENGTH: 265
<212> TYPE: DNA
<213> ORGANISM: Homo sapiens
<220> FEATURE: -
<223> OTHER INFORMATION: 700139953H1

<400> SEQUENCE: 10

```
aggaagccct gcagagcatc agaggcccag ctagagggac aacacagagg agtaatttgc        60
tgacagacct gcagggatgg acctgctttc agctctcaca ctggaaacct gggtcctcct       120
ggcagtcgtc ctggtgctcc tctacggatt tgggacccgc acacatggac ttttcaagaa       180
acagggggatt cctgggccca aacctctgcc ttttttttggc actgtgctga attactatat       240
gggtttatgg aaattcgatg tggag                                              265
```

<210> SEQ ID NO 11
<211> LENGTH: 115
<212> TYPE: DNA
<213> ORGANISM: Homo sapiens
<220> FEATURE: -
<223> OTHER INFORMATION: 700141348H1

<400> SEQUENCE: 11

```
gtaaaagatg tggtccagag aacgtaggaa catgcctgga gagacctaat gtgctcttgt        60
tctgcaaacc catgggcatt atttccctct ccgctcaaga gctcatactg gaagc            115
```

<210> SEQ ID NO 12
<211> LENGTH: 243
<212> TYPE: DNA
<213> ORGANISM: Homo sapiens
<220> FEATURE:
<221> NAME/KEY: unsure
<222> LOCATION: 33
<223> OTHER INFORMATION: a or g or c or t, unknown, or other
<220> FEATURE: -
<223> OTHER INFORMATION: 700141708H1

<400> SEQUENCE: 12

```
tgggcagaaa ggaagccctg cagagcatca gangcccagc tagagggaca acacagagga        60
gtaatttgct gacagacctg caggggatgga cctgctttca gctctcacac tggaaacctg       120
ggtcctcctg gcagtcgtcc tggtgctcct ctacggattt gggacccgca cacatggact       180
tttcaagaaa cagggggattc ctgggcccaa acctctgcct ttttttggca ctgtgctgaa       240
tta                                                                     243
```

<210> SEQ ID NO 13
<211> LENGTH: 249
<212> TYPE: DNA
<213> ORGANISM: Homo sapiens
<220> FEATURE: -
<223> OTHER INFORMATION: 700182318H1

<400> SEQUENCE: 13

```
agagtttcct tttgctcccc aacctgtagt tctaagttca acaaaacagt catcaacaaa      60
agtgacggag gcttccatca gtgtcagggc tctgtgcaga cccagaatcc ctgttccta      120 tgtcatgttc cagcattgta tagcacggtt ccatgtcaca aacagaaagg tcaggaacac     180
tgaggtctgt gaatgtcact gctgcagcga ggtcatgtca ctcctctgtc tactctgtca    240
gtgtcttac                                                             249
```

<210> SEQ ID NO 14
<211> LENGTH: 296
<212> TYPE: DNA
<213> ORGANISM: Homo sapiens
<220> FEATURE:
<221> NAME/KEY: unsure
<222> LOCATION: 22
<223> OTHER INFORMATION: a or g or c or t, unknown, or other
<220> FEATURE: -
<223> OTHER INFORMATION: 700225376H1

<400> SEQUENCE: 14

```
agcaagccta tttctgactg gnctgctgtg cagaatctag accactggca gtgggtgaca      60
gcccagttga ggttaatcga agtctcgtcg caggctctgc tgtaagtctg gcctcttggc    120
ctcacatctt ctttgtggga tccttcccta tctccagctt cctcagctgg tcagggagat    180
ttggtccaga actagaagcc ttaataatct gagcaggtaa gagaggagta aaatgtacag    240
tcttggacat tgactaaagg gtcctgcaga ggatatcaag gtaagtggct tggagg        296
```

<210> SEQ ID NO 15
<211> LENGTH: 169
<212> TYPE: DNA
<213> ORGANISM: Homo sapiens
<220> FEATURE: -
<223> OTHER INFORMATION: 700225757H1

<400> SEQUENCE: 15

```
gctttctggg caagtctatg ttgccctagc tgacccagaa tttgctatat agactattct      60
gtctcaaact cacagaaatt ctcctgcctg tgcctcctga gcgagcacca ggattaaagg    120
cgtgaatcgc tgtccccgtc ttttttcttt cttcttttaa taacccact                 169
```

<210> SEQ ID NO 16
<211> LENGTH: 288
<212> TYPE: DNA
<213> ORGANISM: Homo sapiens
<220> FEATURE: -
<223> OTHER INFORMATION: 700229555H1

<400> SEQUENCE: 16

```
caggagtacc actcacaggc cacctggcag gaagagataa gccccagcc cccgacatcc       60 aggacgcccc gaacctgcca atgtgtgtag ctataccta ttacctcatc atgtgaaata     120
gccaatcata tgtgaacatg tctatgtgcc tcgtttgaat ccaccaatcc ctgtaactat    180
gcatctgctt ctgtacgcct gcttctgctt ccccaatccc tataaaagcc ccatgctgga    240
gctgctgggc gcgcaagtcc tcctaagaga ctgtgtgccc gcagtacc                 288
```

<210> SEQ ID NO 17
<211> LENGTH: 191
<212> TYPE: DNA
<213> ORGANISM: Homo sapiens
<220> FEATURE:
<221> NAME/KEY: unsure
<222> LOCATION: 190
<223> OTHER INFORMATION: a or g or c or t, unknown, or other

```
<220> FEATURE: -
<223> OTHER INFORMATION: 700268788H1

<400> SEQUENCE: 17
cggaggtgct cccaggcggc tgcactggct cggaggagta gcaggaggag ctccgccgca      60
ggaacaaacc tggaggcaaa ccagaaggag gcaatgtttg aatgactgta agaagaccag     120
acagtgaaaa tgtcagccct caactggaag ccctttgtgt acggagggct ggcctccatc     180
aaccgcggan t                                                          191

<210> SEQ ID NO 18
<211> LENGTH: 249
<212> TYPE: DNA
<213> ORGANISM: Homo sapiens
<220> FEATURE:
<221> NAME/KEY: unsure
<222> LOCATION: 45, 118, 128, 163, 245
<223> OTHER INFORMATION: a or g or c or t, unknown, or other
<220> FEATURE: -
<223> OTHER INFORMATION: 700270924H1

<400> SEQUENCE: 18
tgggatcccc aggggctaat gggcatcctg ttcttgcagc agggnactgt gagaaagtct      60
ctcaccgtga ccaagtttct ctgagtgtcc agccaaccca ggctcaccag ctccctcnag     120
ctaccgcncg tccatcaggt caactgccaa ccccaggctg aanaccaaac ccagctatga     180
gctcctggag gcatgactcc ctcagggcca gcagctccga tccctcccag tagtgatcat     240 gggcnaggg                                                             249

<210> SEQ ID NO 19
<211> LENGTH: 306
<212> TYPE: DNA
<213> ORGANISM: Homo sapiens
<220> FEATURE:
<221> NAME/KEY: unsure
<221> NAME/KEY: unsure
<222> LOCATION: 2, 61, 68, 111, 139, 263, (296)...(298), 305
<222> LOCATION:
<223> OTHER INFORMATION: a or g or c or t, unknown, or other
<220> FEATURE: -
<223> OTHER INFORMATION: 700289281H1

<400> SEQUENCE: 19
ancagatccg ggcactggag agggagctgc aagcaggagc agtcaagagt gtggtcagaa      60
ncaccgtnag tggaccagca gggccggctt tttctaccat ggcggcccaa ngctatggct     120
attaccgcac tgtcatatnc acagccatgt tcggaggcta cagcctttac tacttcaacc     180
gcaaaacctt ctcttttgtc atgccctcct tggtggatga gatcgtctg gacaaggacg      240 atttggggc tcatcacgag canccagtcg gcagcctacg catcagcaag tttgtnnncg      300 gggtnt                                                                306

<210> SEQ ID NO 20
<211> LENGTH: 294
<212> TYPE: DNA
<213> ORGANISM: Homo sapiens
<220> FEATURE:
<221> NAME/KEY: unsure
<222> LOCATION: 19, 32, 35, 104, 131, 188, 220
<223> OTHER INFORMATION: a or g or c or t, unknown, or other
<220> FEATURE: -
<223> OTHER INFORMATION: 700291661H1

<400> SEQUENCE: 20
```

```
actagcttct ccagctccnt ctttcccgag angcngcagg gacctcggcc tccagcttac      60
cgggcggatc gaagcagcgg tcgggatggt actgctgggc ttgntgcagt caggcggctc     120
ggtgctcggg naggcgatgg agcaggtgac aggaggcaac ctgctttcca cgctgctcat     180
cgcctgcncc ttcacgctta gccttgtcta cctgttccgn ctcgcagtgg gccacatggt     240
ccagctgccc gctggagcga aaagtccgcc atatatttac tctccaattc cgtc           294
```

<210> SEQ ID NO 21
<211> LENGTH: 295
<212> TYPE: DNA
<213> ORGANISM: Homo sapiens
<220> FEATURE:
<221> NAME/KEY: unsure
<222> LOCATION: 286
<223> OTHER INFORMATION: a or g or c or t, unknown, or other
<220> FEATURE: -
<223> OTHER INFORMATION: 700302454H1

<400> SEQUENCE: 21

```
gcgggccgtg ggtgatctgg tcggtaccgg agagcgcagg ttgtatcacc aacatggggg      60
actctcacga agacaccagt gccaccatgc ctgaggccgt ggctgaagaa gtgtctctat     120
tcagcacgac ggacatggtt ctgttttctc tcatcgtggg ggtcctgacc tactggttca     180
tctttagaaa gaagaaagaa gagataccgg agttcagcaa gatccaaaca acggccccac     240
ccgtcaaaga gagcagcttc gtggaaaaga tgaagaaaac gggaangaac ttatc          295
```

<210> SEQ ID NO 22
<211> LENGTH: 279
<212> TYPE: DNA
<213> ORGANISM: Homo sapiens
<220> FEATURE: -
<223> OTHER INFORMATION: 700303722H1

<400> SEQUENCE: 22

```
gtgactctga gtgtttgagc aggtaacttc tacctttgca cctctatcgc aacaggtcca      60
aaggttccaa aggagctggc aggacactca gacaagatcc actggcttca ggtgtgccta     120
gtcctggagt tcagaaagac ggaggcagct gaatgtggtg ctgaaccaac aacatctagc     180
tacaagggga gccactcctc cacccagcga ctgtgactgt tctcacaggt ctgaatttcc     240
tgttggtatt cacaaagatg cttttttattt ttaacttct                           279
```

<210> SEQ ID NO 23
<211> LENGTH: 183
<212> TYPE: DNA
<213> ORGANISM: Homo sapiens
<220> FEATURE: -
<223> OTHER INFORMATION: 700303922H1

<400> SEQUENCE: 23

```
ggcagcattg atccttatgt atatctgccc tttggaaatg gacccaggaa ctgcattggc      60
atgaggtttg ctctcatgaa tatgaaactg gctctcacta agttctgca aaacttctcc     120 ttccagcctt gtaaggaaac acagatacct ctgaaattaa gcagacaagg acttcttcaa     180
cca                                                                  183
```

<210> SEQ ID NO 24
<211> LENGTH: 286
<212> TYPE: DNA
<213> ORGANISM: Homo sapiens
<220> FEATURE: -
<223> OTHER INFORMATION: 700304405H1

<400> SEQUENCE: 24

| cggaagtgaa ccaaggcact gagcggcatc taatgcacct ggagttggac atctcagact | 60 |
| ccaagatcag gtatgaatct ggagatcacg tggctgtgta cccagccaat gactcagccc | 120 |
| tggtcaacca gattggggag atcctgggag ctgacctgga tgtcatcatg tctctaaaca | 180 |
| atctcgatga ggagtcaaac aagaagcatc cgttcccctg ccccaccacc taccgcacgg | 240 |
| ccctcaccta ctacctggac atcactaacc cgccacgcac caatgt | 286 |

<210> SEQ ID NO 25
<211> LENGTH: 290
<212> TYPE: DNA
<213> ORGANISM: Homo sapiens
<220> FEATURE:
<221> NAME/KEY: unsure
<222> LOCATION: 56
<223> OTHER INFORMATION: a or g or c or t, unknown, or other
<220> FEATURE: -
<223> OTHER INFORMATION: 700305783H1

<400> SEQUENCE: 25

| ctaacagtga atacatagct gcgatcctgg aactcagctc cctcatagtg aaacgncaac | 60 |
| gccagcccctt cctgtacctg gacttcctgt attgcctcac tgctgatggg cggcgcttcc | 120 |
| gcaaggcctg cgacgtggtg cacaacttca cagatgctgt catcagggag agacgcagca | 180 |
| ccctcaatac ccagggcgtt gatgaattcc taaaggccag ggctaagact aaaactttag | 240 |
| actttattga tgttctcttg ctggccaagg atgagcatgg aaggggctg | 290 |

<210> SEQ ID NO 26
<211> LENGTH: 294
<212> TYPE: DNA
<213> ORGANISM: Homo sapiens
<220> FEATURE: -
<223> OTHER INFORMATION: 700306615H1

<400> SEQUENCE: 26

| catccgtggg ctggctcacg ccattcgcct gttcctggag tatacagaca caagctatga | 60 |
| ggacaagaag tacagcatgg gggatgctcc cgactatgac agaagccagt ggctgagtga | 120 |
| gaagttcaaa ctgggcctgg acttccccaa tctgccctac ttaattgatg ggtcacacaa | 180 |
| gatcacccag agcaatgcca tcctgcgcta ccttggccgg aagcacaacc tttgtgggga | 240 |
| gacagaggag gagaggattc gtgtggacgt tttggagaac caggctatgg acac | 294 |

<210> SEQ ID NO 27
<211> LENGTH: 177
<212> TYPE: DNA
<213> ORGANISM: Homo sapiens
<220> FEATURE: -
<223> OTHER INFORMATION: 700329969H1

<400> SEQUENCE: 27

| gctatatcag gagggaccc atgctgtgtc cttctgagat ctaacaggat taaccaatat | 60 |
| gtaaactaga ggaagtggtt ggcctgcact gggcaagccc tctaggactc catccaagaa | 120 |
| agaccagttg gtgttgctct agaggcaaag aaacccataa ggagctggca gtaaaac | 177 |

<210> SEQ ID NO 28
<211> LENGTH: 188
<212> TYPE: DNA
<213> ORGANISM: Homo sapiens
<220> FEATURE:

```
<221> NAME/KEY: unsure
<222> LOCATION: 114, 116
<223> OTHER INFORMATION: a or g or c or t, unknown, or other
<220> FEATURE: -
<223> OTHER INFORMATION: 700368493H1

<400> SEQUENCE: 28
aaagcttccc aatctgtgtg ctcacttggg aggatggcat taggagccag ggctggccat    60 gggtaccttä ctttcctccc tggggtatgc ccaggagaat ggagaaaaaa aaangnttta   120
aagaaaaaat atttaaatt tgatgctggc cttttcaat tgtattgagt aaaagtgttc    180
aagttgtc                                                            188

<210> SEQ ID NO 29
<211> LENGTH: 263
<212> TYPE: DNA
<213> ORGANISM: Homo sapiens
<220> FEATURE: -
<223> OTHER INFORMATION: 700368974H1

<400> SEQUENCE: 29
tccttagctg ggggcggggg gggcagtctg ctactatctg aacgaattta atgtgggagt    60
catgccttat acaacacagg aaattaatgt gtgatctaat gcgtgatcta tgacttatta   120
caatacagga atttaatgtg tgagccatgc cttcaaaaca tgtctagaat ttctggaatt   180
ggccggaagt caacagggat tgcttattta acctttcaaa tcactcattg tgactagggc   240
acatggtctt gcgcttgcta tga                                           263

<210> SEQ ID NO 30
<211> LENGTH: 269
<212> TYPE: DNA
<213> ORGANISM: Homo sapiens
<220> FEATURE:
<221> NAME/KEY: unsure
<222> LOCATION: 129, 133, 153, 163, 165
<223> OTHER INFORMATION: a or g or c or t, unknown, or other
<220> FEATURE: -
<223> OTHER INFORMATION: 700373118H1

<400> SEQUENCE: 30
gtttgaagca gggcgtaggg aaaagcggga ttaaagagta ctacctttat tagctccttc    60
cctccagaat aggtgcaaat ccctccccat gcccatttcc tgccacctgg ggtaaggatg   120
tggcactgnc agnctgtcag cccactgact ttnagtcttc agntngcagt ctgggcaaat   180
accagcgagc tctgttgaac caagaccagg ccttcagagc atctgaacca ctgtggcctt   240
ctctcctcag ccttcactgt ggcttttgc                                     269

<210> SEQ ID NO 31
<211> LENGTH: 288
<212> TYPE: DNA
<213> ORGANISM: Homo sapiens
<220> FEATURE:
<221> NAME/KEY: unsure
<222> LOCATION: 159
<223> OTHER INFORMATION: a or g or c or t, unknown, or other
<220> FEATURE: -
<223> OTHER INFORMATION: 700375521H1

<400> SEQUENCE: 31
gcagccatgg atcgcgggga ggaacctctg tccgcgaggc cggcgctgga gaccgagagc    60
ctgcgattcc tgcacgtcac agtgggctcc ctgctggcca gctatggctg gtacatcctc   120
ttcagctgcg tccttctcta cattgtcatc cagaagctnt ccctgcgact gagggctttä   180
```

```
aggcagaggc agctggacca agctgaggct gttctggagc ctgatgttgt tgttaagcga    240
caagaggctt tagcagctgc tcgtttgaga atgcaggaag atctgaat                 288

<210> SEQ ID NO 32
<211> LENGTH: 255
<212> TYPE: DNA
<213> ORGANISM: Homo sapiens
<220> FEATURE:
<221> NAME/KEY: unsure
<222> LOCATION: 156, 157
<223> OTHER INFORMATION: a or g or c or t, unknown, or other
<220> FEATURE: -
<223> OTHER INFORMATION: 700376694H1

<400> SEQUENCE: 32
ttatgattat caattttaca taacattaat attatatcaa acctccttaa gaaaatgagt    60
atggatgttc acagtatgtt tgattttat ctacaagaat gaatctgatt cagaatgctt     120
ttcagctgac atacagagca ctaaatactt taaggnnaac cataggtctg aatctcttaa    180
gaattctcag tctctatggg atgtaggac gcattataaa tgcattaatc cttatagtca    240
atcctgtgcc tagga                                                     255

<210> SEQ ID NO 33
<211> LENGTH: 271
<212> TYPE: DNA
<213> ORGANISM: Homo sapiens
<220> FEATURE:
<221> NAME/KEY: unsure
<222> LOCATION: 25, 64, 70, 82, 102, 155
<223> OTHER INFORMATION: a or g or c or t, unknown, or other
<220> FEATURE: -
<223> OTHER INFORMATION: 700480077H1

<400> SEQUENCE: 33
ctgacctgac ccatgatgta agggnccgta ggggagcatc accactgcaa aggctgacta    60
aggnctgttn ggctaaaggt cnctttgaag cccagtgtct anagtcacac cttctttgct    120
ctgggcccag gaggcctact tcttctttt ctcgnggaat cctggaatct taaagataaa    180
agaacctaga aagaaaatca aacccacttt ccttgtgggg cagatggtaa tatgggactg    240
agaacagcaa acctggggtc ttggagagga g                                   271

<210> SEQ ID NO 34
<211> LENGTH: 256
<212> TYPE: DNA
<213> ORGANISM: Homo sapiens
<220> FEATURE:
<221> NAME/KEY: unsure
<222> LOCATION: 70
<223> OTHER INFORMATION: a or g or c or t, unknown, or other
<220> FEATURE: -
<223> OTHER INFORMATION: 700483259H1

<400> SEQUENCE: 34
gtgacgtaca tggaaaacaa agcctacggg gacaggctca agccgcagac agcagcaagt    60
aaagcgcctn cggccctgaa gcatggcagc tatcccttcc agcggctcgc tcgtggctac    120
ccatgactac tatcggcgta agtagcccct cgcagcccc gcccagggct ggcccagggc    180
tctgtggctg accgcctcc ccttcccagg acgtctgggc tcctcgtcca gcaacagctc    240
cggcggaagt gcagag                                                    256

<210> SEQ ID NO 35
```

```
<211> LENGTH: 259
<212> TYPE: DNA
<213> ORGANISM: Homo sapiens
<220> FEATURE:
<221> NAME/KEY: unsure
<222> LOCATION: 219
<223> OTHER INFORMATION: a or g or c or t, unknown, or other
<220> FEATURE: -
<223> OTHER INFORMATION: 700483475H1

<400> SEQUENCE: 35
ctctcgtact tcggcaatgg ctggattccc accgtcatca cggcctttgt ccttgctacc      60
tcccaggccc aagctggatg gctacaacat gattatggcc acctttctgt ctataagaaa     120
tccatatgga accacattgt ccacaagttt gtcattggcc acttaaaggg tgcctccgcc     180
aactggtgga accatcgaca tttccagcac catgcgaanc caacatcttc cacaaggacc     240
ccgacataaa gagcctgca                                                  259

<210> SEQ ID NO 36
<211> LENGTH: 284
<212> TYPE: DNA
<213> ORGANISM: Homo sapiens
<220> FEATURE:
<221> NAME/KEY: unsure
<221> NAME/KEY: unsure
<222> LOCATION: 16, 25, 54, 63, 68, 70, 80, 141, 154, 210, 275
<222> LOCATION:
<223> OTHER INFORMATION: a or g or c or t, unknown, or other
<220> FEATURE: -
<223> OTHER INFORMATION: 700483803H1

<400> SEQUENCE: 36
gaggaacgcc gccgcntcgc tcggnatcct acaccaatca ggaagctgct gtcnagccat      60 ggnggganang agaagccan ctcaagaggc tgacgtggaa cccatggtaa catcaggggc     120
ctcagaagca gtgccaaggg ngctttctgg aganccctcag aacatctctg atgtagatgc     180
cttcaacttg ctcctggaga tgaaactgan acgacggcgt gaggtcccaa ccttccatgt     240
actgtgaccc agctagtggc cgaggatggc agcanggtgt atgt                      284

<210> SEQ ID NO 37
<211> LENGTH: 258
<212> TYPE: DNA
<213> ORGANISM: Homo sapiens
<220> FEATURE: -
<223> OTHER INFORMATION: 700502844H1

<400> SEQUENCE: 37
ggcagacctt agcagattct ggatgccatc agtgactgaa gccattaagg agactcggct      60
ggagtagcag ctaagaggac agagagacaa gggctacgag gcagcaatat aaacagatct     120
ggtgttgctg agatttgaga cgaaggtttc ccatggcttc ttttcacatc cgccagttcc     180
aggagaggga ctatgaacag gtcgtggata tgttctccag gggaatgaag gaacacatcc     240
ccactgcctt ccgccact                                                   258

<210> SEQ ID NO 38
<211> LENGTH: 250
<212> TYPE: DNA
<213> ORGANISM: Homo sapiens
<220> FEATURE: -
<223> OTHER INFORMATION: 700503415H1

<400> SEQUENCE: 38
gtagctttcc cctttgctg gcacagaagt ctgtccatct gcaagcgctt tggaacacag       60
```

```
actgcctgga gccaccttcc tttgggagac cttcctgcct cagctgtcgt cctgtgtcgt      120
cattcactaa agctcctgac gtcagattaa gcaagcagtg atgggttaca ttagagacaa      180
gccgcagaga taaggcctgt tgctgtttcg cagataatga tgagttttaa ttacccactg      240
gtttgtatgg                                                             250
```

<210> SEQ ID NO 39
<211> LENGTH: 271
<212> TYPE: DNA
<213> ORGANISM: Homo sapiens
<220> FEATURE:
<221> NAME/KEY: unsure
<222> LOCATION: 218, 228, 255, 270
<223> OTHER INFORMATION: a or g or c or t, unknown, or other
<220> FEATURE: -
<223> OTHER INFORMATION: 700504333H1

<400> SEQUENCE: 39

```
gtttattttg acacagacat ggacaaagcg atggagcgct atgtctctat gcccaaggaa      60
aaggctccag aacacattcc ccttctcttc attgccttcc catcaagcaa ggatccaacc     120
tgggaggacc gattcccaga ccgatccaca atgactgtgc tggtacccac ggcctttgaa     180
tggttcgagg agtggcagga ggagcctaag ggcaagcnaa gtgttgcntt ggaaccctca     240
aaaaaacttc ccggnaaccc tttatggggn a                                     271
```

<210> SEQ ID NO 40
<211> LENGTH: 267
<212> TYPE: DNA
<213> ORGANISM: Homo sapiens
<220> FEATURE:
<221> NAME/KEY: unsure
<222> LOCATION: 14, 20, 22, 24, 81, 248, 253
<223> OTHER INFORMATION: a or g or c or t, unknown, or other
<220> FEATURE: -
<223> OTHER INFORMATION: 700510534H1

<400> SEQUENCE: 40

```
tgaaagcgta aggncttgcn tntnagaggc tctgtagtga gttctgtttg cctataaggg      60
aagtggaaca accgagacac ncgcacttct ttcgagtgtt aaggagcctg ggaggagcag     120
gcagccgctt gctttgagca tgctcaggtg gggctgtccg ccgctgtggg gaaggcaccc     180
tgcagcaggg cttcctgccc cacctctcca ttgtagtagt gtccagatct cagaaacgca     240
gcttgaancc agnttcaaag gtaccag                                         267
```

<210> SEQ ID NO 41
<211> LENGTH: 278
<212> TYPE: DNA
<213> ORGANISM: Homo sapiens
<220> FEATURE:
<221> NAME/KEY: unsure
<221> NAME/KEY: unsure
<222> LOCATION: 40, 44, (53)...(55), 60, 69, 72, 74, 159, 234
<222> LOCATION:
<223> OTHER INFORMATION: a or g or c or t, unknown, or other
<220> FEATURE: -
<223> OTHER INFORMATION: 700514914H1

<400> SEQUENCE: 41

```
ccactgcagc gccccccccc aaagatggaa agattctgcn ttancttcat atnnncttan      60
aacatttgna cncnattctt taactttaga atctccccta gagcctgttc ttctttaaac     120 acccttatg ctggagtagg atgatggctg agtttcttna aaagagctta aatatagagt      180
```

```
cacaaacatg agatagatgc ctgccgccca ctctttccac aaactcgaga accncttttgt        240 gcacgcagct gccatggaag gaaatcctgg ggcttctt                                 278
```

<210> SEQ ID NO 42
<211> LENGTH: 308
<212> TYPE: DNA
<213> ORGANISM: Homo sapiens
<220> FEATURE: -
<223> OTHER INFORMATION: 700519169H2

<400> SEQUENCE: 42

```
cccaatcttt taagactttt cataatgatg ttaagaccag ggcagactat ctactggcca         60
tggactgcag ccaggagatg ccctgcccct cctgggacct gcacaccacc tctctgggga        120
acttgacaaa ggtccctaag gctaagggag gtctccttcc tactaggtcc ctgactttga        180
ctctgtggtt ctctaggaac cgtgtgcaca cttgtctctg ttgtaaccac aaagggcagt        240
agcacctagc atgtcatgtc ctgccccggc tgcttgcctc ccacccaccc aggattctct        300
gggctggc                                                                 308
```

<210> SEQ ID NO 43
<211> LENGTH: 273
<212> TYPE: DNA
<213> ORGANISM: Homo sapiens
<220> FEATURE: -
<223> OTHER INFORMATION: 700528082H1

<400> SEQUENCE: 43

```
ataaaagtga aaactgggca agggcagggg gctgggcgtg aaccgcttac tagataatgt         60
tctctaaaaa ttggctctga aaaccctgtt tgtgtattcg ttttatgagt gcttaaaaat        120
ggtgtgacca gggcatggtc actgtcattg aacagcaac  atgcttgctg gtcacattgg        180 aatgggggaaa tgtgaagaaa gctggacatc aggcctgcgg cacccatttc tttgtatgaa       240
agtgttgtgt acaaaccccc cactaatcat ttt                                     273
```

<210> SEQ ID NO 44
<211> LENGTH: 290
<212> TYPE: DNA
<213> ORGANISM: Homo sapiens
<220> FEATURE:
<221> NAME/KEY: unsure
<222> LOCATION: 58, 157
<223> OTHER INFORMATION: a or g or c or t, unknown, or other
<220> FEATURE: -
<223> OTHER INFORMATION: 700535328H1

<400> SEQUENCE: 44

```
ggtctgacca agtgagaaag acagcagggg cacccaggcc tcagacactc tggcgtantc         60
ccaaagaaag atggccacag cccagctccc tggtaccaag ctgtcatccc taaactctgc        120
tctgtgcccc ttgtgggcag acgttaatca agccctngcc ctttctgatg ggcccctcca        180
tcccgggaac actaaaaggt agtcttactg tccaccaccc tacacctgtt ttcataagtt        240
atgcacaaat gcgaacagct gagacagaga tggagaagtt cttcgttttg                   290
```

<210> SEQ ID NO 45
<211> LENGTH: 124
<212> TYPE: DNA
<213> ORGANISM: Homo sapiens
<220> FEATURE:
<221> NAME/KEY: unsure
<222> LOCATION: 34, 53, 87, 109, 122
<223> OTHER INFORMATION: a or g or c or t, unknown, or other

```
<220> FEATURE: -
<223> OTHER INFORMATION: 700535905H1

<400> SEQUENCE: 45
cctacctctg gtggaaaaag tacatcactc aggngcagct ggtccagttt gtngctgaca      60
atcatccaga ccagctgcgg ggtcatntgg ccgtgctcct tccctctcng gtggctgtac     120 tncc                                                                  124

<210> SEQ ID NO 46
<211> LENGTH: 262
<212> TYPE: DNA
<213> ORGANISM: Homo sapiens
<220> FEATURE:
<221> NAME/KEY: unsure
<222> LOCATION: 148
<223> OTHER INFORMATION: a or g or c or t, unknown, or other
<220> FEATURE: -
<223> OTHER INFORMATION: 700593984H1

<400> SEQUENCE: 46
gggaaagtgt gttctgaggg ccctgtgggg ccaaggggga ccagcctcac attccacacg      60
tgcgccactc tgcttggagc ctatttattt tgtatttatt tgaacagagt tatgtcctaa     120 ctattttttat agatttgttt aattaatncc ctgtcatttt caagttcatt tttttttattc   180 atatttatgt tcatggttga ttgtacctcc tgtcaccagc tggtggggca ggggagacaa     240
ggtagaaagt ggccacagag tg                                              262

<210> SEQ ID NO 47
<211> LENGTH: 275
<212> TYPE: DNA
<213> ORGANISM: Homo sapiens
<220> FEATURE:
<221> NAME/KEY: unsure
<222> LOCATION: 17
<223> OTHER INFORMATION: a or g or c or t, unknown, or other
<220> FEATURE: -
<223> OTHER INFORMATION: 700607183H1

<400> SEQUENCE: 47
cacagcccct accagcncac cctccataac tgcaccaaga ggatctatcc aacacctccc      60
tgagcaggag gagcctgaag actccaaggg aaagagtcct gaggaaccct ttcctgtgca     120
gctggatcta accacaaacc cacagggtga cacactggat gtctccttcc tctacctgga     180
gcctgaggaa aagaaactgg tggtcctgcc tttccctggg aaggaacagc gctcccctga     240
gtgcccgggg cccgaaaagc aaagaacccc ctgat                                275

<210> SEQ ID NO 48
<211> LENGTH: 285
<212> TYPE: DNA
<213> ORGANISM: Homo sapiens
<220> FEATURE:
<223> OTHER INFORMATION: 700607235H1

<400> SEQUENCE: 48
ctgaagaccc accatgtctc tgctgactac tgtactactt ctctggggtt tcattctggg      60
cccagcaact gacacagcct gtatattcaa ggaagcctcg gaaaacagtc ccttgcccag     120
gccctggctt tctgccaatc cagtgccctg gatcacacct ggcctgagga cattcctgct     180
gtgccagggg acagtgcggg atgtagtctt catgctgagg cggaaggag atgatggttt      240 cctggcgata gtccaacaga tgttttttctg gagggagctg gaccc                    285
```

<210> SEQ ID NO 49
<211> LENGTH: 267
<212> TYPE: DNA
<213> ORGANISM: Homo sapiens
<220> FEATURE:
<221> NAME/KEY: unsure
<222> LOCATION: 36, 37, 223
<223> OTHER INFORMATION: a or g or c or t, unknown, or other
<220> FEATURE: -
<223> OTHER INFORMATION: 700607844H1

<400> SEQUENCE: 49

```
ctcgatcgtc cagacccccac ggcgtcacca tgctgnncca tgatcaggaa ctcactgttc      60
gggagcgtgg agacgtggcc ttggcaggtt ttaagcaccg ggggcaagga agacgtctcc     120
tatgaggaaa gagcctgcga aggggggaaag tttgctactg tggaagtgac agacaaacct    180
gtggatgagg ctctccggga agcaatgccc aagatcatga agncgtgggg ggcaccaatg    240
acaaaggagt cggcatggga atgacag                                         267
```

<210> SEQ ID NO 50
<211> LENGTH: 267
<212> TYPE: DNA
<213> ORGANISM: Homo sapiens
<220> FEATURE:
<221> NAME/KEY: unsure
<222> LOCATION: 6, 77, 128, 143, 146
<223> OTHER INFORMATION: a or g or c or t, unknown, or other
<220> FEATURE: -
<223> OTHER INFORMATION: 700607873H1

<400> SEQUENCE: 50

```
gaaganacac caaagctcac tcactcttca ggttctcact gaacctactg tatcggaagg      60
gacttcacct cccagangtc catttttatg aagactgttg agacagcttt ccagaaacta    120
gaaccatntg gaagatagac ctnggngtat tcctgtgcgg attatcttga ttacgttaat    180
taattctgga tgggactagg ctaaagtgtc atcatgattt tccattaaca aggtgcacag    240
atgctacaaa tggctgggag aaatcct                                         267
```

<210> SEQ ID NO 51
<211> LENGTH: 276
<212> TYPE: DNA
<213> ORGANISM: Homo sapiens
<220> FEATURE: -
<223> OTHER INFORMATION: 700608519H1

<400> SEQUENCE: 51

```
caccacactg catctgccct acatgccacc ttacaccatc atctatttcc cctcccgagg      60
tgtggcctca gcgttttcaa gatgaagggc acaagccata gtcactcctg gggaacccct    120
caacactggt gctggaggga tgtggccaag accacgttgg gggcaagacc gagacttggg    180
gcgggactac aattgtggtt ggtggggcca ggactgacct cttagcctcc ataggcagct    240
acactgtctg tcacttttcc tccttccctg tgccgg                               276
```

<210> SEQ ID NO 52
<211> LENGTH: 293
<212> TYPE: DNA
<213> ORGANISM: Homo sapiens
<220> FEATURE:
<221> NAME/KEY: unsure
<222> LOCATION: 16, 179
<223> OTHER INFORMATION: a or g or c or t, unknown, or other
<220> FEATURE: -
<223> OTHER INFORMATION: 700609074H1

<400> SEQUENCE: 52

```
ggcgtggagt tggagnagag cgtcaggcgc ctccgggaga agtttcatgg aaaagtgtcc      60
cccaagaagg cagggctct tatgaggaag tttggcagcg accacactgg agttgggcgc     120
tctatcgtgt acgggctcaa gcagaaagat ggacaggagc tgagcaacga tttggacgnc    180
caggacccac cagaggacat gaagcaggac caagatatcc aggcagtagc cacctctctg    240
ttgcccctga cgcaagccaa tcttcgaatg ttccaaagag cccaagatga cct            293
```

<210> SEQ ID NO 53
<211> LENGTH: 288
<212> TYPE: DNA
<213> ORGANISM: Homo sapiens
<220> FEATURE:
<221> NAME/KEY: unsure
<222> LOCATION: 66, 138, 152, 236, 242, 252, 253, 279
<223> OTHER INFORMATION: a or g or c or t, unknown, or other
<220> FEATURE: -
<223> OTHER INFORMATION: 700609967H1

<400> SEQUENCE: 53

```
ctgcctcgca gccccgagcg cgcgcctctc cagctcccgc tccggcttcc ccaaccaggc      60
ttattntggc tcccgacccg gtgcagaccc ctgaccggc ctccgcccag ctccgccaaa    120
tgcgctactt tacttggnag gaggtggcgc angctccggg agggagaagg agcgatggct    180
cgtaatcgac cggaaggtgt acaacatcag cgacttcagt tcgccgccac ccgggnggct    240
cncgggtcat cnnccactag ctggtcagga tgccacggna tcctttgt                288
```

<210> SEQ ID NO 54
<211> LENGTH: 258
<212> TYPE: DNA
<213> ORGANISM: Homo sapiens
<220> FEATURE:
<221> NAME/KEY: unsure
<222> LOCATION: 53, 244
<223> OTHER INFORMATION: a or g or c or t, unknown, or other
<220> FEATURE: -
<223> OTHER INFORMATION: 700626839H1

<400> SEQUENCE: 54

```
gggtgcgcgt ggagttgcgc atgcgccttc ccgccgcgca gggcaaaggt ggnggcgctc      60
tggtgaatgg ttggttgctg tgcaagagcg ttttctggct tttggtggcg aaggcggcct    120
ggccgcgagg tgcagctgct ggtgggcagg tgtactaatg tctacagact atgagctttc    180
agaatctctg gagagagtac aaagttctgc atgttatggt acctttaatc gggttcatac    240
attngggtgg cacagaat                                                  258
```

<210> SEQ ID NO 55
<211> LENGTH: 268
<212> TYPE: DNA
<213> ORGANISM: Homo sapiens
<220> FEATURE:
<221> NAME/KEY: unsure
<222> LOCATION: 7, 11, 40, 53, 150
<223> OTHER INFORMATION: a or g or c or t, unknown, or other
<220> FEATURE: -
<223> OTHER INFORMATION: 700627890H1

<400> SEQUENCE: 55

```
gtacaangag ngccggggct tgggtctagt tggaggggan gcagtggcca gtncagggct      60
cagatgagag agttagccga gttaggggca gctactagga tgggggcagg aggagaagcg    120
```

-continued

```
gggctaacta taaagaagac tagatttcgn cacagtgggt atgtggaagg cagctttcaa      180 accgccttg tcaaacaaca cagggccagc agccttcaag accaggctat ccctgccgtc       240
tgctggcatg ggggcacttg taccgtcc                                         268

<210> SEQ ID NO 56
<211> LENGTH: 265
<212> TYPE: DNA
<213> ORGANISM: Homo sapiens
<220> FEATURE:
<221> NAME/KEY: unsure
<222> LOCATION: 62, 264
<223> OTHER INFORMATION: a or g or c or t, unknown, or other
<220> FEATURE: -
<223> OTHER INFORMATION: 700629293H1

<400> SEQUENCE: 56
atgaccttta acttttctaa aaatgtgaag ttttgtactt atatatatca gctaaagtat        60
tntagcattc tttagtgtac ttagtttgat gccactttta gtgtttttgt tgcttttgtc      120
tgatttttat gaatgttcat tttaagactc cttgttgaaa tgggacagtt tcgttctttg      180
ataagcccga gaagaggatt cccttgggtg ttgacctcct ctgcatgatg tgcccaagca      240
tctgaactgc aaccaaggcc tttnc                                            265
```

MARKERS FOR PEROXISOMAL PROLIFERATORS

FIELD OF THE INVENTION

The present invention relates to a composition for use in detecting toxicological effects of test compounds or therapeutic treatments and methods employing such compositions.

BACKGROUND OF THE INVENTION

Toxicity testing is a necessary and time-consuming part of the pharmaceutical drug development pipeline. A more rapid screen to detect toxicity of lead drug candidates may be the use of gene expression microarrays. For example, microarrays consisting of full length genes or gene fragments on a substrate may be formed. These arrays can then be tested with samples treated with the drug candidates to elucidate the gene expression pattern associated with treatment with the drug candidate. This gene pattern can be compared with gene expression patterns of compounds associated with known toxicological responses.

Benzo(a)pyrene is a known rodent and likely human carcinogen and is the prototype of a class of compounds, the polycyclic aromatic hydrocarbons. It is metabolized by several forms of cytochrome P450 and associated enzymes to both activated and detoxified metabolites (Dogawa et al (1994) Cancer Res. 54: 4915–4919). The ultimate metabolites are the bay-region diol epoxide, benzo(a)pyrene-7,8-diol-9,10-epoxide (BPDE) and the K-region diol epoxide, 9-hydroxy benzo(a)pyrene-4,5-oxide, which have been shown to cause DNA adduct formation (alkylation of guanine bases). DNA adducts have been shown to persist in rat liver up to 56 days following treatment with benzo(a)pyrene at a dose of 10 mg/kg body weight 3 times per week for 2 weeks (Qu and Stacey, (1996) Carcinogenesis 17: 53–59).

Acetaminophen is a widely-used analgesic. It is metabolized by specific cytochrome P450 isozymes with the majority of the drug undergoing detoxification by glucuronic acid, sulfate and glutathione conjugation pathways (Chen. et al. (1998) Chem. Res. Toxicol. 11: 295–301). However, at high nontherapeutic doses, acetaminophen can cause hepatic and renal failure by being metabolized to an active intermediate, N-acetyl-p-benzoquinone imine (NAPQI). NAPQI then binds to sulfhydryl groups of proteins causing their inactivation and leading to subsequent cell death (Kroger et al. Gen. Pharmacol. (1997) 28: 257–263).

Clofibrate is an antilipidemic drug which lowers elevated levels of serum triglycerides. In rodents, chronic treatment produces hepatomegaly, an increase in hepatic peroxisomes (Lock et al. (1989) Ann. Rev. Pharmacol. Toxicol. 29: 145–163). Clofibrate has been shown to increase levels of cytochrome P450 4A and reduce the levels of P450 4F (Kawashima et al. (1997) Arch. Biochem. Biophys. 347: 148–154). It is also involved in transcription of β-oxidation genes as well as induction of peroxisome proliferator activated receptors (Arch. Biochem. Biophys. (1997) 347: 148–154).

The present invention provides compositions and methods for the screening, preferably in a microarray format, of compounds and therapeutic treatments for toxicological effects.

SUMMARY OF THE INVENTION

In one aspect, the invention provides a method for screening a compound for a toxicological effect. The method comprises selecting a plurality of polynucleotide targets, wherein the polynucleotide targets have first gene expression levels altered in tissues treated with known toxicological agents when compared with untreated tissues. Some of the first gene expression levels may be upregulated and others downregulated when associated with a toxicological response. A sample is treated with the compound to induce second gene expression levels of a plurality of polynucleotide probes. Then first and second gene expression levels are compared to identify those compounds that induce expression levels of the polynucleotide probes that are similar to those of the polynucleotide targets and the similarity of expression levels correlates with a toxicological effect of the compound.

Preferably, the comparing comprises (i) contacting the polynucleotide targets with the polynucleotide probes under conditions effective to form hybridization complexes between the polynucleotide targets and the polynucleotide probes; and (ii) detecting the presence or absence of the hybridization complexes. In this context, similarity may mean that at least 1, preferably at least 5, more preferably at least 10, of the upregulated polynucleotide targets form hybridization complexes with the polynucleotide probes at least once during a time course to a greater extent than would the probes derived from a sample not treated with the test compound or a known toxicological agent. Similarity may also mean that at least 1, preferably at least 3, of the downregulated polynucleotide target sequences form hybridization complexes with the polynucleotide probes at least once during a time course to a lesser extent than would the probes of a sample not treated with the test compound or a known toxicological agent.

Preferred tissues are selected from the group consisting of liver, kidney, brain, spleen, pancreas and lung. Preferred toxicological agents are selected from the group consisting of hypolipidemic drugs, n-alkylcarboxylic acids, n-alkylcarboxylic acid precursors, azole antifungal compounds, leukotriene D4 antagonists, herbicides, pesticides, phthalate esters, phenyl acetate, dehydroepiandrosterone sulfate, oleic acid, methanol and their corresponding metabolites. The polynucleotide targets comprise genes that are upregulated-or-down regulated at least 2.5 fold, preferably at least 3 fold, in tissues treated with known toxicological agents when compared with untreated tissues. Preferred polynucleotide targets are selected from the group consisting of SEQ ID NOs: 1–56, or fragments thereof, some of whose expression is upregulated and others of whose expression is downregulated. Even more preferable are SEQ ID NOs: 2, 3, 16, 18, 29, 43, 52, and 55 which are upregulated and SEQ ID NOs: 9, 10, 11, 12, 13, 14, 15, 22, 23, 30, 33, 35, 45, 47, 50, and 53 which are downregulated. In one embodiment, the polynucleotide targets are hybridizable array elements of a microarray.

Alternatively, the invention provides methods for screening a therapeutic treatment for a toxicological effect or for screening a sample for a toxicological response to a compound or therapeutic treatment.

In another aspect, the invention provides methods for preventing a toxicological response by administering complementary nucleotide sequences against one or more selected upregulated polynucleotide targets or a ribozyme that specifically cleaves such sequences. Alternatively, a toxicological response may be prevented by administering sense nucleotide sequences for one or more selected downregulated polynucleotide targets.

In yet another aspect, the invention provides methods for preventing a toxicological response by administering an agonist which initiates transcription of a gene comprising a downregulated polynucleotide of the invention. Alternatively, a toxicological response may be prevented by administering an antagonist which prevents transcription of a gene comprising an upregulated polynucleotide of the invention.

DESCRIPTION OF THE SEQUENCE LISTING

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

The Sequence Listing contains the sequences of exemplary polynucleotide targets of the invention, SEQ ID NOs: 1–56.

DESCRIPTION OF THE INVENTION

Definitions

The term "microarray" refers to an ordered arrangement of hybridizable array elements. The array elements are arranged so that there are preferably at least one or more different array elements, more preferably at least 10 array elements, and most preferably at least 100 array elements, and even more preferably 10,000, on a 1 $cm^2$ substrate surface. Furthermore, the hybridization signal from each of the array elements is individually distinguishable. In a preferred embodiment, the array elements comprise polynucleotide sequences.

A "polynucleotide" refers to a chain of nucleotides. Preferably, the chain has from about 5 to 10,000 nucleotides, more preferably from about 50 to 3,500 nucleotides. The term "polynucleotide target" refers to a polynucleotide sequence capable of hybridizing with a "polynucleotide probe" to form a polynucleotide target/probe complex under hybridization conditions. In some instances, the sequences will be complementary (no mismatches) when aligned. In other instances, there may be a substantial mismatch, up to 10%.

A "plurality" refers preferably to a group of one or more members, preferably to a group of at least about 10, and more preferably to a group of at least about 100 members, even more preferably a group of 10,000 members.

The term "gene" or "genes" refers to the partial or complete coding sequence of a gene. The term also refers to 5' or 3' untranslated regions. The gene may be in a sense or antisense configuration.

The term "upregulated" refers to messenger RNA levels encoding a gene which are detectably increased in a tissue sample from a treated animal compared with the messenger RNA levels encoding the same gene in a tissue sample from an untreated animal.

The term "downregulated" refers to messenger RNA levels encoding a gene which are detectably decreased in a tissue sample from a treated animal compared with the messenger RNA levels encoding the same gene in a tissue sample from an untreated animal.

"Toxicological agent or compound" is any compound that elicits an unfavorable response in an individual or animal, such as DNA damage, organ damage, cell damage or cell death.

A "fragment" refers to a sequence which is a portion of a polynucleotide target sequence. Exemplary fragments are sequences comprising nucleotides 1–20 of SEQ. ID NOs: 1–56.

The Invention

The present invention provides a composition and method for screening test compounds or therapeutic treatments for toxicological effects. Additionally the invention provides methods for characterizing the toxicological responses of a sample to a test compound or a therapeutic treatment. In particular, the present invention provides a composition comprising a plurality of polynucleotide sequences derived from normal rat liver cDNA libraries, normalized rat liver cDNA libraries and prehybridized rat liver cDNA libraries and rat kidney libraries. The polynucleotide sequences have been further selected for exhibiting upregulated-or-downregulated gene expression in rat liver samples when the rat liver samples have been exposed to a known toxin, in particular a peroxisomal proliferator (PP). PPs include hypolipidemic drugs, such as clofibrate, clofenic acid, nafenopin, gemfibrozil, ciprofibrate, fenofibrate, bezafibrate, halofenate, simfibrate, benzofibrate, etofibrate, WY-14,643, and the like; nalkylcarboxylic acids, such as trichloroacetic acid, valproic acid, hexanoic acid, and the like; n-alkylcarboxylic acid precursors, such as trichloroethylene, etrachloroethylene, and the like; azole antifungal compounds, such as bifenazole, and the like; leukotriene D4 antagonists; herbicides; pesticides; phthalate esters, such as di-[2-ethylhexyl] phthalate, mono-[2-ethylhexyl] phthalate, and the like; and natural chemicals, such as phenyl acetate, dehydroepiandrosterone sulfate, oleic acid, methanol, and the like. In a preferred embodiment the toxin is clofibrate, or one of its toxic metabolites. The extent of upregulation or downregulation is at least 2.5 fold, more preferably at least 3 fold.

Exemplary polynucleotide sequences (targets) include SEQ ID NOs: 1–56 provided in the Sequence Listing or fragments thereof. These and other polynucleotide sequences can be immobilized on a substrate and used as hybridizable array elements in a microarray format. The microarray may be used to characterize gene expression patterns associated with novel compounds to elucidate any toxicological effects or to monitor the effects of therapeutic treatments where toxicological effects may be expected.

When the polynucleotide targets are employed as hybridizable array elements in a microarray, the array elements are organized in an ordered fashion so that each element is present at a specified location on the substrate. Because the array elements are at specified locations on the substrate, the hybridization patterns and intensities (which together create a unique expression profile) can be interpreted in terms of expression levels of particular genes and can be correlated with a toxicological effect associated with a compound or a therapeutic treatment.

Furthermore, the present invention provides methods for screening compounds and/or therapeutic treatments for potential toxicological effects and for screening a sample's toxicological response to a particular test compound. Briefly, these methods entail treating a sample with the compound to be tested to elicit a change in gene expression patterns comprising the expression of a plurality of polynucleotide probes. Polynucleotide targets are selected by identifying those genes in rat liver or kidney that are upregulated-or-downregulated at least 2.5 fold, more preferably at least 3 fold, when treated with a known toxic compound. Then, the polynucleotide targets and probes are combined under conditions effective to form hybridization complexes which may be detected by methods well known in the art. Detection of higher or lower levels of such hybridization complexes compared with hybridization complexes derived from samples treated with a compound that is known not to induce a toxicological effect correlates with a toxicological effect of a test compound or a toxicological response to a therapeutic treatment.

Sequences are identified that reflect all or most of the genes that are expressed in rat liver or kidney. Sequences may be identified by isolating clones derived from several types of rat cDNA libraries, including normal rat cDNA libraries, normalized rat cDNA libraries and prehybridized rat cDNA libraries. Clone inserts derived from these clones may be partially sequenced to generate expressed sequence tags (ESTs).

In one embodiment, two collections of ESTs are identified and sequenced. A first collection of ESTs (the originator sequences) are derived from rat liver and kidney and are derived from the cDNA libraries presented in the Examples. A second collection includes ESTs derived from other rat cDNA libraries available in the ZooSeq database (Incyte Pharmaceuticals).

The two collections of ESTs are screened electronically to form master clusters of ESTs. Master clusters are formed by identifying overlapping EST sequences and assembling these ESTs. A nucleic acid fragment assembly tool, such as the Phrap tool (WashU-Merck) and the GELVIEW Fragment Assembly system (GCG), can be used for this purpose. The minimum number of clones necessary to constitute a cluster is two. In another embodiment, a collection of human genes implicated in toxicology are used as the originator sequences and the collect-on of ESTs derived from the 55 rat cDNA libraries are again used as the additional sequences. Master clusters are formed around specific originator sequences, including the ESTs identified in rat liver and kidney or GenBank sequences which code for polypeptides implicated in toxicology in humans.

After the sequences have been clustered, the most 5' clone is selected. After assembling the sequences, a representative clone is nominated from each master cluster. The most 5' clone is usually preferred because it is the one most likely to contain the complete gene. The nomination process is described in greater detail in "Relational Database and System for Storing Information Relating to Biomolecular Sequences and Reagents, Ser. No. 09/034,807, filed Mar. 4, 1998, herein incorporated in its entirety by reference. These sequences may be used as array elements on a microarray.

Then, samples are treated, preferably at subchronic doses, with one or more known toxicological agents over a defined time course. Preferably, the agents are peroxisomal proliferators.

The gene expression patterns derived from such treated biological samples can be compared with the gene expression patterns derived from untreated biological samples to identify genes whose expression is either upregulated or downregulated due to the presence of the toxins. These sequences may then be employed as array elements in a microarray alone or in combination with other array element sequences. Such a microarray is particularly useful to detect and characterize gene expression patterns associated with known toxicological agents. Such gene expression patterns can then be used for comparison to identify other compounds or therapeutic treatments which also elicit a toxicological response.

The selected polynucleotide sequences can be manipulated further to optimize the performance of the polynucleotide sequences as hybridization sequences. Some sequences may not hybridize effectively under hybridization conditions due to secondary structure. To optimize probe hybridization, the probe sequences are examined using a computer algorithm to identify portions of genes without potential secondary structure. Such computer algorithms are well known in the art, such as OLIGO 4.06 Primer Analysis Software (National Biosciences) or LASERGENE software (DNASTAR). These programs can search nucleotide sequences to identify stem loop structures and tandem repeats and to analyze G+C content of the sequence (those sequences with a G+C content greater than 60% are excluded). Alternatively, the sequences can be optimized by trial and error. Experiments can be performed to determine whether sequences and complementary target polynucleotides hybridize optimally under experimental conditions.

The polynucleotide sequences can be any RNA-like or DNA-like material, such as mRNAs, cDNAs, genomic DNA, peptide nucleic acids, branched DNAs and the like. The polynucleotide sequences can be in sense or antisense orientations.

In one embodiment, the polynucleotide sequences are cDNAs. The size of the DNA sequence of interest may vary, and is preferably from 50 to 10,000 nucleotides, more preferably from 150 to 3,500 nucleotides. In a second embodiment, the polynucleotide sequences are vector DNAs. In this case the size of the DNA sequence of interest, i.e., the insert sequence, may vary from about 50 to 10,000 nucleotides, more preferably from about 150 to 3,500 nucleotides.

The polynucleotide sequences can be prepared by a variety of synthetic or enzymatic schemes which are well known in the art. (Caruthers et al. (1980) *Nucleic Acids Symp. Ser.* (7): 215–223). Nucleotide analogues can be incorporated into the polynucleotide sequences by methods well known in the art. The only requirement is that the incorporated nucleotide analogues must serve to base pair with polynucleotide probe sequences. For example, certain guanine nucleotides can be substituted with hypoxanthine which base pairs with cytosine residues. However, these base pairs are less stable than those between guanine and cytosine. Alternatively, adenine nucleotides can be substituted with 2,6-diaminopurine which can form stronger base pairs than those between adenine and thymidine. Additionally, the polynucleotide sequences can include nucleotides that have been derivatized chemically or enzymatically. Typical modifications include derivatization with acyl, alkyl, aryl or amino groups.

The polynucleotide sequences can be immobilized on a substrate via chemical bonding. Furthermore, the sequences do not have to be directly bound to the substrate, but rather can be bound to the substrate through a linker group. The linker groups are typically about 6 to 50 atoms long to provide exposure to the attached polynucleotide probe. Preferred linker groups include (ethylene glycol oligomers, diamines, diacids and the like. Reactive groups on the substrate surface react with one of the terminal portions of the linker to bind the linker to the substrate. The other terminal portion of the linker is then functionalized for binding the polynucleotide probe. Preferred substrates are any suitable rigid or semirigid support, including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which the polynucleotide sequences are bound. Preferably, the substrates are optically transparent.

The samples can be any sample comprising polynucleotide probes and obtained from any bodily fluid (blood, urine, saliva, phlegm, gastric juices, etc.), cultured cells, biopsies, or other tissue preparations. The samples can be derived from humans or animal models.

DNA or RNA can be isolated from the sample according to any of a number of methods well known to those of skill in the art. For example, methods of purification of nucleic acids are described in *Laboratory Techniques in Biochemistry and Molecular Biology: Hybridization With Nucleic Acid Probes, Part I. Theory and Nucleic Acid Preparation,* P. Tijssen, ed. Elsevier (1993). In one preferred embodiment, total RNA is isolated using the TRIZOL total RNA isolation reagent (Life Technologies, Inc.) and mRNA is isolated using oligo d(T) column chromatography or glass beads. When polynucleotide probes are amplified it is desirable to amplify the nucleic acid sample and maintain the relative abundances of the original sample, including low abundance transcripts. RNA can be amplified in vitro, in situ or in vivo (See Eberwine U.S. Pat. No. 5,514,545).

It is also advantageous to include quantitation controls within the sample to assure that amplification and labeling procedures do not change the true distribution of polynucleotide probes in a sample. For this purpose, a sample is spiked with a known amount of a control polynucleotide and the composition of polynucleotide sequences includes reference polynucleotide sequences which specifically hybridize with the control target polynucleotides. After hybridization and processing, the hybridization signals obtained should reflect accurately the amounts of control polynucleotide added to the sample.

Prior to hybridization, it may be desirable to fragment the polynucleotide probes. Fragmentation improves hybridization by minimizing secondary structure and cross-hybridization to other polynucleotide probes in the sample or noncomplementary polynucleotide sequences. Fragmentation can be performed by mechanical or chemical means.

The polynucleotide probes may be labeled with one or more labeling moieties to allow for detection of hybridized probe/target polynucleotide complexes. The labeling moieties can include compositions that can be detected by spectroscopic, photochemical, biochemical, bioelectronic, immunochemical, electrical, optical or chemical means. The labeling moieties include radioisotopes, such as $^{32}P$, $^{33}P$ or $^{35}S$, chemiluminescent compounds, labeled binding proteins, heavy metal atoms, spectroscopic markers, such as fluorescent markers and dyes, magnetic labels, linked enzymes, mass spectrometry tags, spin labels, electron transfer donors and acceptors, and the like. Preferred fluorescent markers include Cy3 and Cy5 (Amersham Pharmacia Biotech).

Hybridization causes a polynucleotide probe and a complementary target polynucleotide to form a stable duplex through base pairing. Hybridization methods are well known to those skilled in the art (See, for example, *Laboratory Techniques in Biochemistry and Molecular Biology,* Vol. 24: *Hybridization With Nucleic Acid Probes,* P. Tijssen, ed. Elsevier, N.Y. (1993)). Conditions can be selected for hybridization where only fully complementary target and polynucleotide probe hybridize, i.e., each base pair must interact with its complementary base pair. Alternatively, conditions can be selected where target and polynucleotide sequences have mismatches but are still able to hybridize. Suitable conditions can be defined by salt concentration, temperature, and other chemicals and conditions well known in the art. Varying additional parameters, such as hybridization time, the concentration of detergent or solvent, and the inclusion or exclusion of carrier DNA, are well known to those skilled in the art. Salt concentration may be less than about 750 mM NaCl and 75 mM trisodium citrate, preferably less than about 500 mM NaCl and 50 mM trisodium citrate, and most preferably less than about 250 mM NaCl and 25 mM trisodium citrate. Stringent temperature conditions will ordinarily include temperatures of at least about 22° C., more preferably of at least about 37° C., and most preferably of at least about 42° C. Additional variations on these conditions will be readily apparent to those skilled in the art (Wahl, G. M. and S. L. Berger (1987) Methods Enzymol. 152: 399–407; Kimmel, A. R. (1987) Methods Enzymol. 152: 507–511; Ausubel, F. M. et al. (1997) *Short Protocols in Molecular Biology,* John Wiley & Sons, New York, N.Y.; and Sambrook, J. et al. (1989) *Molecular Cloning, A Laboratory Manual,* Cold Spring Harbor Press, Plainview, N.Y.).

More particularly, hybridization can be performed with buffers, such as 5× SCC/0.1% SDS at 60° C. for about 6 hours. Subsequent washes are performed at higher stringency with buffers, such as 1× SCC/0.1% SDS at 45° C., then 0.1× SCC at 45° C. to retain hybridization of only those target/probe complexes that contain exactly complementary sequences.

Hybridization specificity can be evaluated by comparing the hybridization of specificity-control polynucleotide sequences to specificity-control polynucleotide probes that are added to a sample in a known amount. The specificity-control target polynucleotides may have one or more sequence mismatches compared with the corresponding polynucleotide sequences. In this manner, whether only complementary target polynucleotides are hybridizing to the polynucleotide sequences or whether mismatched hybrid duplexes are forming is determined.

Hybridization reactions can be performed in absolute or differential hybridization formats. In the absolute hybridization format, polynucleotide probes from one sample are hybridized to the sequences in a microarray format and signals detected after hybridization complex formation correlate to polynucleotide probe levels in a sample. In the differential hybridization format, the differential expression of a set of genes in two biological samples is analyzed. For differential hybridization, polynucleotide probes from both biological samples are prepared and labeled with different labeling moieties. A mixture of the two labeled polynucleotide probes is added to a microarray. The microarray is then examined under conditions in which the emissions from the two different labels are individually detectable. Sequences in the microarray that are hybridized to substantially equal numbers of polynucleotide probes derived from both biological samples give a distinct combined fluorescence (Shalon et al. PCT publication WO95/35505). In a preferred embodiment, the labels are fluorescent labels with distinguishable emission spectra, such as Cy3 and Cy5 fluorophores.

After hybridization, the microarray is washed to remove nonhybridized nucleic acids and complex formation between the hybridizable array elements and the polynucleotide probes is detected. Methods for detecting complex formation are well known to those skilled in the art. In a preferred embodiment, the polynucleotide probes are labeled with a fluorescent label and measurement of levels and patterns of fluorescence indicative of complex formation is accomplished by fluorescence microscopy, preferably confocal fluorescence microscopy.

In a differential hybridization experiment, polynucleotide probes from two or more different biological samples are labeled with two or more different fluorescent labels with different emission wavelengths. Fluorescent signals are detected separately with different photomultipliers set to detect specific wavelengths. The relative abundances/expression levels of the polynucleotide probes in two or more samples is obtained.

Typically, microarray fluorescence intensities can be normalized to take into account variations in hybridization intensities when more than one microarray is used under similar test conditions. In a preferred embodiment, individual polynucleotide probe/target complex hybridization intensities are normalized using the intensities derived from internal normalization controls contained on each microarray.

The composition comprising a plurality of polynucleotide target sequences can be used as hybridizable elements in a microarray. Such a microarray can be employed to identify expression profiles associated with particular toxicological responses. Then, a particular subset of these polynucleotide targets can be identified whose expression is altered in response to a particular toxicological agent. These polynucleotides can be employed to identify other compounds with a similar toxicological response.

Alternatively, for some treatments with known side effects, the microarray, and expression patterns derived therefrom, is employed to "fine tune" the treatment regimen. A dosage is established that minimizes expression patterns associated with undesirable side effects. This approach may be more sensitive and rapid than waiting for the patient to show toxicological side effects before altering the course of treatment.

Generally, the method for screening a compound or therapeutic treatment to identify those with a potential toxicological effect entails selecting a plurality of polynucleotide targets genes whose gene expression levels are altered in tissues treated with known toxicological agents when compared with untreated tissues. Then a sample is treated with the compound or therapeutic treatment to induce a pattern of gene expression comprising the expression of a plurality of polynucleotide probes. A test compound may be screened at several doses to determine doses which may be toxic and other doses that may not.

Then, the expression levels of the polynucleotide targets and the polynucleotide probes are compared to identify those compounds that induce expression levels of the polynucleotide probes that are similar to those of the polynucleotide targets. In one preferred embodiment, gene expression levels are compared by contacting the polynucleotide targets with the polynucleotide probes under conditions effective to form hybridization complexes between polynucleotide targets and polynucleotide probes; and detecting the presence or absence of the hybridization complexes.

Similarity may mean that at least 1, preferably at least 5, more preferably at least 10, of the upregulated polynucleotide targets form hybridization complexes with the polynucleotide probes at least once during a time course to a greater extent than would the probes of a sample not treated with the test compound. Similarity may also mean that at least 1, preferably at least 3, of the downregulated polynucleotide target sequences form hybridization complexes with the polynucleotide probes at least once during a time course to a lesser extent than would the probes of a sample not treated with the test compound.

Such a similarity of expression patterns means that a toxicological effect is associated with the compound or therapeutic treatment tested. Preferably, the toxicological agents belong to the class of peroxisomal proliferators, including hypolipidemic drugs, such as clofibrate, clofenic acid, nafenopin, gemfibrozil, ciprofibrate, fenofibrate, bezafibrate, halofenate, simfibrate, benzofibrate, etofibrate, WY-14,643, and the like; n-alkylcarboxylic acids, such as trichloroacetic acid, valproic acid, hexanoic acid, and the like; n-alkylcarboxylic acid precursors, such as trichloroethylene, etrachloroethylene, and the like; azole antifungal compounds, such as bifenazole, and the like; leukotriene D4 antagonists; herbicides; pesticides; phthalate esters, such as di-[2-othylhexyl] phthalate, mono-[2-ethylhexyl] phthalate, and the like; and natural chemicals, such as phenyl acetate, dehydroepiandrosterone sulfate, oleic acid, methanol, and the like. Of particular interest is the study of the toxic effects of these compounds on the liver, kidney, brain, spleen, pancreas and lung.

It is understood that this invention is not limited to the particular methodology, protocols, and reagents described, as these may vary. It is also understood that the terminology used herein is for the purpose of describing particular embodiments only, and is not intended to limit the scope of the present invention which will be limited only by the appended claims. The examples below are provided to illustrate the subject invention and are not included for the purpose of limiting the invention.

I cDNA Library Construction

The RALINOT01 library was constructed from liver tissue removed from a pool of fifty 10- to 11-week-old Sprague-Dawley female rats (Charles River Laboratories, Wilmington, Mass.). The animals were housed in standard laboratory caging and fed PMI-certified Rodent Diet #5002. The animals appeared to be in good health at the time of tissue harvest. The animals were anesthetized by $CO_2$ induction, and then cardiocentesis was performed.

Frozen tissue was homogenized and lysed in TRIZOL reagent (1 g tissue/10 ml TRIZOL; Life Technologies, Inc), a monophasic solution of phenol and guanidine isothiocyanate, using a Brinkmann Homogenizer Polytron PT-3000 (Brinkmann Instruments, Westbury, N.Y.). After a brief incubation on ice, chloroform (1:5 v/v) was added and mixed, and then centrifuged at 1,000 rpm. The upper aqueous layer was removed to a fresh tube and the RNA precipitated with isopropanol, resuspended in DEPC-treated water, and treated with DNase for 25 min at 37° C. The RNA was re-extracted once with phenol-chloroform, pH 4.7, and precipitated using 0.3 M sodium acetate and 2.5 volumes ethanol. The mRNA (poly(A+) RNA) was then isolated using an OLIGOTEX kit (QIAGEN, Inc., Chatsworth, Calif.) and used to construct the cDNA library.

The mRNA was handled according to the recommended protocols in the SuperScript Plasmid System for cDNA Synthesis and Plasmid Cloning (Gibco/BRL). The cDNAs were fractionated on a Sepharose CL4B column (Amersham Pharmacia Biotech), and those cDNAs exceeding 400 bp were ligated into the plasmid pINCY1 (Incyte Pharmaceuticals, Inc., Palo Alto, Calif.). The plasmid pINCY1 was subsequently transformed into DH5α™ competent cells (Cat. #18258-012; Gibco/BRL).

The RAKINOT01 library was constructed using poly(A+) RNA isolated from kidney tissue removed from a pool of fifty, 7- to 8-week-old male Sprague-Dawley rats, as described above.

The PAKINOT02 library was constructed using poly(A+) RNA isolated from kidney tissue removed from a pool of fifty, 10- to 11-week-old female Sprague-Dawley rats, as described above.

II cDNA Library Normalization

In some cases, cDNA libraries were normalized in a single round according to the procedure of Soares et al. (1994, Proc. Natl. Acad. Sci. USA 91: 9228–9232) with the following modifications. The primer to template ratio in the primer extension reaction was increased from 2:1 to 10:1. The dNTP concentration in the reaction was reduced to 150 $\mu$M each dNTP, allowing the generation of longer (400–10000 nt) primer extension products. The reannealing hybridization was extended from 13 to 19 hours. The single stranded DNA circles of the normalized library were purified by hydroxyapatite chromatography and converted to partially double-stranded by random priming, follower by electroporation into DH10B competent bacteria (Gibco/BRL).

The Soares normalization procedure is designed to reduce the initial variation in individual cDNA frequencies to achieve abundances within one order of magnitude while maintaining the overall sequence complexity of the library. In the normalization process, the prevalence of high-abundance cDNA clones decreases significantly, clones with mid-level abundance are relatively unaffected, and clones for rare transcripts are effectively increased in abundance. In the modified Soares normalization procedure, significantly longer hybridization times are used which allows for the increase of gene discovery rates by biasing the normalized libraries toward low-abundance cDNAs that are well represented in a standard transcript image.

The RALINON03 normalized rat liver library was constructed with $2.0 \times 10^6$ independent clones from the RALINOT01 library. Starting RNA was made from liver tissue removed from a pool of fifty, 10- to 11-week-old female Sprague-Dawley rats. The library was normalized in one round using conditions adapted from Soares et al., supra, except that a significantly longer (48-hour) reannealing hybridization was used.

The PALINON04 normalized rat liver library was constructed with $4.6 \times 10^5$ independent clones from the RALINOT01 library. Starting RNA was made from liver tissue removed from a pool of fifty, 10- to 11-week-old female Sprague-Dawley rats.

The RALINON07 normalized rat liver library was constructed with $2.0 \times 10^5$ independent clones from the PALINOT01 library. Starting RNA was made from liver tissue removed from a pool of fifty, 10- to 11-week-old female Sprague-Dawley rats.

III cDNA Library Prehybridization

The RALINOH01 library was constructed with clones from the RALINOT01 library. Starting RNA was made from liver tissue removed from a pool of fifty, 10- to 11-week-old female Sprague-Dawley rats. After preparation of the cDNA library, 9,984 clones were spotted onto a nylon filter, incubated, and processed to bind plasmid DNA to the filter. 10 ml of pre-warmed hybridization buffer per were added. The filter was hybridized in 0.75 M NaCl, 0.1 M $Na_2HPO_4$/$NaH_2PO_4$, 0.15 M Tris-HCl (pH 7.5), 5× Denhardt's Solution, 2% SDS, 100 µg/ml sheared salmon sperm DNA, 50% formamide, and [$^{32}$P]-labeled oligonucleotide sequences made from RALINOT01, at 42° C. for 14–16 hours. Then, filters were rinsed with 200 ml of 2× SSC at room temperature for 5 minutes. Filters were washed for 30 minutes at 68° C. with 200 ml of pre-warmed wash 1 (2× SSC, 1% SDS). A second wash was performed for an additional 30 minutes at 68° C. Filters were then washed twice with pre-warmed wash 2 (0.6× SSC, 1% SDS) for 30 minutes at 68° C. 4,224 clones had very low hybridization signals and were selected for sequencing. About 20% of the clones do not have signals and these are isolated and sequenced.

IV Isolation and Sequencing of cDNA Clones

DNA was isolated using the following protocol. Single bacterial colonies were transferred into individual wells of 384-well plates (Genetix Ltd, Christchurch, UK) using sterile toothpicks. The wells contained 1 ml of sterile Terrific Broth (Catalog #22711, Life Technologies, Inc.) with 25 mg/l carbenicillin and 0.4% glycerol (v/v). The plates were covered and placed in a Thermodyne incubator (Newtown Square, Pa.) at 37° C. for 8–10 hours prior to use. Plasmid DNA was released from the cells and amplified using direct link PCR (RaD, V.B. (1994) Anal. Biochem. 216: 1–14) as follows. The direct link PCR solution included 30 ml of Nucleix Plus PCR nucleotide mix (Catalog #4577235, Amersham Pharmacia Biotech) and 300 µl of Taq DNA polymerase (Catalog #0303Z, Amersham Pharmacia Biotech) with 12 µl Pfu DNA polymerase (Stratagene). Five µl of the PCR solution were added to each of the 384 wells using the MICROLAB 2200 system (Hamilton, Reno, Nev.); plates were centrifuged at 1000 rpm for 20 seconds and refrigerated until use. A 384 pin tool (V&P Scientific Inc, San Diego, Calif.) was used to transfer bacterial cells from the incubation plate into the plate containing the PCR solution where the component 0.1° Tween 20 caused the cells to undergo lysis and release the plasmid DNA. After lysis, the plates were centrifuged up to 500 rpm, covered with a cycle sealer, and cycled using a 384-well Peltier Thermal Cycler (MJ PTC 200, MJ Research, Watertown, Mass.) using the program dPCR30 with the following parameters: Step 1) 95° C., 1 minute; Step 2) 94° C., 30 seconds; Step 3) 55° C., 30 seconds; Step 4) 72° C., 2 minutes; Step 5) steps 2, 3, and 4 repeated 29 times; Step 6) 72° C., 10 minutes; and Step 7) storage at 4° C.

The concentration of DNA in each well was determined by dispensing 100 µl Pico Green Dye Mix (0.25% (v/v) Pico Green Dye) (Molecular Probes, Eugene, OR) dissolved in 1× TE and 0.5 µl of undiluted PCR product into each well of an opaque fluorimeter plate (Corning Costar, Acton, Mass.), allowing the DNA to bind to Pico Green Dye. The plate was scanned in a Flouroscan II (Labsystems Oy, Helsinki, FI) to measure the fluorescence of the sample and to quantitate the concentration of DNA. Typical concentrations of each DNA sample were in the range of 100 to 500 ng/ml.

The cDNAs were sequenced by the method of Sanger, F. and A. R. Coulson (J. Mol. Biol. (1975) 94: 441–448), using either a HYDRA microdispenser (Robbins Scientific, Sunnyvale, Calif.) or MICROLAB 2200 (Hamilton) in combination with Peltier Thermal Cyclers (PTC200 from MJ Research, Watertown, Mass.) and ABI 377 DNA Sequencing Systems (Perkin Elmer). Most of the isolates were sequenced according to standard ABI protocols, using ABI kits (Cat. #79345, 79339, 79340, 79357, 79355). Typically, 500 to 700 base pairs were sequenced in 3.5 to 4 hours. The solution volumes were used at 0.25×–1.0× concentrations. In the alternative, cDNAs may have been sequenced using solutions and dyes from Amersham Pharmacia Biotech.

The sequences derived from the sequencing of the clone inserts were used to populate the Zooseq database (Incyte Pharmaceuticals, Inc.).

V Rat Liver and Kidney Gene Selection

As a first step, originator sequences from high throughput sequencing experiments were derived from clone inserts from RALINOT01, RAKINOT01, RAKINOT02, RALINOH01, RALINON03, RALINON04 and RALINON07. cDNA library clones were obtained. There were 18,140 rat liver sequences and 5,779 rat kidney sequences.

Additionally, 1,500 rat sequences derived from clone inserts of any of 55 rat cDNA libraries were selected based on their homology to genes coding for polypeptides implicated in toxicological responses including peroxisome-associated genes, lysosome-associated genes, apoptosis-associated genes, P450 cytochromes, sulfotransferases, cysteine proteases, and the like.

Then, all the remaining sequences derived from all of the rat cDNA library clones were clustered based on the originator sequences described above. The clustering process involved identifying overlapping sequences that have a match quality indicated by a product score of 50 using BLAST. 6581 master clusters were identified.

After forming the clone clusters, a consensus sequence was generated based on the assembly of the clone sequences using Phrap. The assembled sequences were then annotated by first screening the assembled sequences against GenBank using BLASTn and then by screening the assembled sequences against GenPept using FASTX. About two thirds of the assembled sequences were annotated, about one third of the assembled sequences were not annotated.

VI Microarray Preparation

Clones nominated in the process described in Example VI were used to generate array elements. Each array element was amplified from bacterial cells. PCR amplification used primers complementary to the vector sequences flanking the cDNA insert. Array elements were amplified in thirty cycles of PCR from an initial quantity of 1–2 ng to a final quantity greater than 5 µg. Amplified array elements were then purified using Sephacryl-400 (Amersham Pharmacia Biotech, Piscataway, N.J.).

Purified array elements were immobilized on polymer-coated glass slides. Glass microscope slides (Corning, Corning, N.Y.) cleaned by ultrasound in 0.1% SDS and acetone, with extensive distilled water washes between and after treatments. Glass slides were etched in 4% hydrofluoric acid (VWR, West Chester, Pa.), washed extensively in distilled water, and coated with 0.05% aminopropyl silane (Sigma Aldrich, St. Louis, Mo.) in 95% ethanol. Coated slides were cured in a 110° C. oven.

Array elements were applied to the coated glass substrate using a procedure described in U.S. Pat. No. 5,807,522 and incorporated herein by reference. In brief, 1 µl of the array element DNA, at an average concentration of 0.5 µg/ml in 3× SSC, was loaded into the open capillary printing element by a high-speed robotic apparatus. The apparatus then deposited about 5 nl of array element sample per slide. A total of 7404 array elements representing rat liver and kidney genes and a variety of control elements, including 14 synthetic control sequences, human genomic DNA, and yeast genomic DNA, were arrayed in four identical quadrants within a 1.8 cm² area of the glass substrate.

Microarrays were UV-crosslinked using a STRATALINKER UV-crosslinker (Stratagene, La Jolla, Calif.). Microarrays were washed at room temperature once in 0.2, SDS and three times in distilled water. Non-specific binding sites were blocked by incubation of microarrays in 0.2% casein in phosphate buffered saline (PBS) (Tropix Inc., Bedford, Mass.) for 30 minutes at 60° C. followed by washes in 0.2% SDS and distilled water as before.

VII Probe Preparation

Male Sprague-Dawley rats (6–8 wk old) were dosed intraperitoneally with either clofibrate (Acros, Geel, Belgium) at 250 mg/kg body weight (bw), or dimethylsulfoxide vehicle (DMSO; Acros) at less than 2 ml/kg bw. Animals were monitored daily for physical condition and body weight, and blood samples were assayed for serum alanine transferase (ALT) and aspartate aminotransferase (AST) levels using a diagnostic kit (Sigma Aldrich). Three animals per group were sacrificed approximately 12 hours (h), 24 h, 3 days (d), 7 d, 14 d, and 28 d following the last dose administered. Observed gross pathology and liver weights were recorded at time of necropsy. Liver, kidney, brain, spleen and pancreas from each rat were harvested, flash frozen in liquid nitrogen, and stored at −80° C.

Frozen Liver was homogenized and lysed in TRIZOL reagent (Cat. #10296-028; Life Technologies, Inc, Gaithersburg, Md.) following the modifications for liver RNA isolation. Poly(A+) RNA was isolated using an OLIGOTEX kit (QIAGEN, Inc., Chatsworth, Calif.) and labeled with either Cy3 or Cy5-labeled primers (Operon Technologies, Alameda, Calif.) using the GEMBRIGHT labeling kit (Incyte). mRNA isolated from tissues of rats dosed with clofibrate was labeled with Cy5 and mRNA isolated from tissues of rats dosed with DMSO was labeled with Cy3. Quantitative and differential expression pattern control cDNAs were added to each labeling reaction. Labeled cDNA was treated with 0.5 M sodium bicarbonate (pH 9.2) for 20 min at 85° C. to degrade the RNA and purified using two successive CHROMA SPIN 30 gel filtration spin columns (Clontech, Palo Alto, Calif.). Cy3 labeled control sample and Cy5 labeled experimental sample were combined and precipitated in glycogen, sodium acetate, and ethanol.

VIII Hybridization

Hybridization reactions contained 9 µl of probe mixture consisting of 0.2 µg each of both Cy3 and Cy5 labeled cDNA synthesis products in 5× SSC, 0.2% SCS hybridization buffer. The probe mixture was heated to 65° C. for 5 minutes and was aliquoted onto the microarray surface and covered with an 1.8 cm² coverslip. The arrays were transferred to a waterproof chamber having a cavity just slightly larger than a microscope slide. The chamber was kept at 100% humidity internally by the addition of 140 µl of 5× SSC in a corner of the chamber. The chamber containing the arrays was incubated for about 6.5 hours at 60° C. The arrays were washed for 10 min at 45° C. in low stringency wash buffer (1× SSC, 0.1% SDS), three times for 10 minutes each at 45° C. in high stringency wash buffer (0.1× SSC), and then dried.

IX Detection

The microscope used to detect the reporter-labeled hybridization complexes was equipped with an Innova 70 mixed gas 10 W laser (Coherent Lasers, Santa Clara, Calif.) capable of generating spectral lines at 488 nm for excitation of Cy3, and 632 nm for excitation of Cy5. The excitation laser light was focused on the array using a 20× microscope objective (Nikon). The slide containing the array was placed on a computer-controlled X-Y stage on the microscope and raster-scanned past the objective. The 1.8 cm×1.8 cm array used in the present example was scanned with a resolution of 20 micrometers.

In two separate scans, a mixed gas multiline laser excited the two fluorophores sequentially. Emitted light was split, based on wavelength, into two photomultiplier tube detectors (PMT R1477, Hamamatsu Photonics, San Jose, Calif.) corresponding to the two fluorophores. Appropriate filters positioned between the array and the photomultiplier tubes were used to filter the signals. The emission maxima of the fluorophores used were 565 nm for Cy3 and 650 nm for Cy5. Each array was typically scanned twice, one scan per fluorophore using the appropriate filters at the laser source, although the apparatus was capable of recording the spectra from both fluorophores simultaneously.

The sensitivity of the scans was typically calibrated using the signal intensity generated by a cDNA control species added to the probe mix at a known concentration. A specific Location on the array contained a complementary DNA sequence, allowing the intensity of the signal at that location to be correlated with a weight ratio of hybridizing species of 1:100,000. When two probes from different sources (e.g., representing test and control cells), each labeled with a different fluorophore, are hybridized to a single array for the purpose of identifying genes that are differentially expressed, the calibration was done by labeling samples of the calibrating cDNA with the two fluorophores and adding identical amounts of each to the hybridization mixture.

The output of the photomultiplier tube was digitized using a 12-bit RTI-835H analog-to-digital (A/D) conversion board (Analog Devices, Norwood, Mass.) installed in an IBM-compatible PC computer. The digitized data were displayed as an image where the signal intensity was mapped using a linear 20-color transformation to a pseudocolor scale ranging from blue (low signal) to red (high signal). The data was also analyzed quantitatively. Where two different fluorophores were excited and measured simultaneously, the data were first corrected for optical crosstalk (due to overlapping emission spectra) between the fluorophores using each fluorophore's emission spectrum.

A grid was superimposed over the fluorescence signal image such that the signal from each spot was centered in each element of the grid. The fluorescence signal within each element was then integrated to obtain a numerical value corresponding to the average intensity of the signal. The software used for signal analysis was the GEMTOOLS gene expression analysis program (Incyte).

X Results

The expression patterns of three cytochrome P450 isozymes known to be induced in a toxicological response were monitored during the 28 day time course. The results are shown in Table 1.

TABLE 1

Gene expression patterns of known genes

| Gene | 12 hours | 1 day | 3 days | 7 days | 28 days |
|---|---|---|---|---|---|
| P450 LA-omega | 15 | 26 | 2.0 | 2.1 | 3.0 |
| P450 4A | 6.5 | 16.5 | 2.1 | 3.0 | 3.5 |
| P450 3A | 0.14 | 1.6 | 0.63 | 0.50 | 0.45 |

Each of the three genes was upregulated greater than 3 fold at least once during the time course.

We have discovered novel gene sequences that are up-regulated or downregulated at least 3 fold at least once during the time course. These sequences are SEQ ID NOs: 1–56 provided in the Sequence Listing. These polynucleotide sequences can be used for screening compounds or therapeutic treatments for a toxicologic effect. Table 2 shows the gene expression pattern of selected sequences that were upregulated at least 3 fold at least once during the time course.

TABLE 2

Gene expression patterns of upregulated polynucleotide targets

| SEQ ID NO: | 12 hours | 1 day | 3 days | 7 days | 28 days |
|---|---|---|---|---|---|
| 2 | 11.6 | 14.4 | 2.4 | 3.0 | 3.2 |
| 3 | 11.6 | 18.7 | 3.0 | 3.3 | 3.8 |
| 16 | 1.2 | 2.8 | 1.0 | 2.3 | 4.8 |
| 18 | 0.9 | 1.9 | 0.9 | 1.5 | 4.5 |
| 29 | 4.3 | 1.1 | 1.6 | 1.7 | 5.7 |
| 43 | 5.1 | 1.2 | 1.7 | 1.8 | 6.0 |
| 52 | 4.8 | 1.4 | 2.0 | 1.5 | 2.4 |
| 55 | 5.1 | 1.3 | 1.9 | 1.8 | 5.5 |

Table 3 shows the gene expression pattern of selected sequences that were downregulated at least 3 fold at least once during the time course.

TABLE 3

Gene expression patterns of downregulated polynucleotide targets

| SEQ ID NO: | 12 hours | 1 day | 3 days | 7 days | 28 days |
|---|---|---|---|---|---|
| 9 | 0.15 | 1.4 | 1.0 | 0.77 | 0.67 |
| 10 | 0.13 | 1.2 | 0.83 | 0.63 | 0.56 |
| 11 | 0.13 | 0.56 | 0.37 | 1.0 | 1.2 |
| 12 | 0.13 | 1.1 | 0.91 | 0.71 | 0.56 |
| 13 | 0.11 | 0.67 | 0.36 | 1.0 | 1.2 |
| 14 | 0.14 | 0.63 | 0.59 | 1.1 | 0.29 |
| 15 | 0.16 | 0.67 | 0.71 | 1.2 | 0.32 |
| 22 | 0.33 | 0.14 | 1.1 | 0.83 | 1.2 |
| 23 | 0.14 | 1.2 | 1.0 | 0.77 | 0.71 |
| 30 | 0.16 | 0.67 | 0.53 | 1.1 | 1.4 |
| 33 | 0.43 | 0.18 | 0.40 | 0.34 | 0.23 |
| 35 | 0.06 | 0.71 | 0.42 | 1.1 | 1.2 |
| 45 | 0.22 | 1.5 | 0.77 | 1.7 | 1.3 |
| 47 | 0.19 | 0.45 | 1.0 | 1.3 | 1.8 |
| 50 | 0.12 | 0.48 | 1.2 | 1.0 | 1.2 |
| 53 | 0.14 | 0.91 | 0.56 | 1.5 | 1.4 |

What is claimed is:

1. A method for detecting a toxicological effect of a test compound associated with increased or decreased levels of a polynucleotide sequence in a sample comprising:
   a) treating a sample with a toxin;
   b) obtaining a polynucleotide sequence from the sample treated with the toxin;
   c) contacting the polynucleotide sequence with an array comprising a combination of polynucleotides comprising SEQ ID NOs. 1–56 under conditions effective to form one or more hybridization complexes;
   d) detecting the hybridization complexes, wherein the presence, absence or change in amount of the hybridization complex, as compared with the hybridization complexes formed by SEQ ID NOs:1–56 with polynucleotide sequence from an untreated sample, is indicative of a toxicological response to the toxin; then
   e) measuring the level of polynucleotide sequences in a sample treated with a test compound using the method of steps (c) and (d); and
   f) comparing the level detected in step (e) with the level detected in step (c) wherein an increase or decrease in the level detected in step (e) indicates a toxicological response to the test compound.

2. The method of claim 1, wherein the sample is a tissue selected from the group consisting of liver, kidney, brain, spleen, pancreas and lung.

3. The method of claim 1, wherein the toxin is selected from the group consisting of hypolipidemic drugs, n-alkylcarboxylic acids, n-alkylcarboxylic acid precursors, azole antifungal compounds, leukotriene D4 antagonists, herbicides, pesticides, phthalate esters, phenyl acetate, dehydroepiandrosterone sulfate, oleic acid, methanol and their corresponding metabolites.

4. The method of claim 1, wherein the test compound which elicits the toxicological response induces at least a 2.5 fold change in the amount of the hybridization complexes formed between the polynucleotide of the array with at least one of the polynucleotide sequences of the sample, when compared with polynucleotide sequences of an untreated sample.

5. The method of claim 1 wherein the test compound which elicits the toxicological response is a compound not known to induce a toxicological response.

6. An isolated and purified polynucleotide selected from the group consisting of SEQ ID NOs:4–6, 8–10, 18–20, 23, 25, 27–30 32, 33, 36–39, 41–47, 49, and 51.

7. A method of using a polynucleotide as a polynucleotide probe, the method comprising:
   a) combining the polynucleotide of claim 6 with a polynucleotide target under conditions to allow formation of a complex; and
   b) detecting the complex, thereby identifying a polynucleotide target which forms a complex with the polynucleotide of claim 6.

8. The method of claim 7 wherein the polynucleotide target is selected from the group consisting of mRNA, cDNA, genomic DNA, peptide nucleic acids, and branched DNA.

* * * * *

UNITED STATES PATENT AND TRADEMARK OFFICE
CERTIFICATE OF CORRECTION

PATENT NO. : 6,160,104
DATED : Dec. 12, 2000
INVENTOR(S) : Mary Jane Cunningham, Gary B. Zweiger, Scott R. Panzer, Jeffrey J. Seilhamer It is certified that error appears in the above-identified patent and that said Letters Patent are hereby corrected as shown below:

Col 47, line 51, (Claim 1), delete "step (c)" and insert --step (d)--

Signed and Sealed this

Twenty-ninth Day of May, 2001

Attest:

NICHOLAS P. GODICI

Attesting Officer

Acting Director of the United States Patent and Trademark Office